United States Patent
Koerzdoerfer et al.

(10) Patent No.: US 11,073,585 B2
(45) Date of Patent: Jul. 27, 2021

(54) LOW-FIELD MAGNETIC RESONANCE FINGERPRINTING

(71) Applicant: Siemens Healthcare GmbH, Erlangen (DE)

(72) Inventors: Gregor Koerzdoerfer, Erlangen (DE); Mathias Nittka, Baiersdorf (DE); Peter Speier, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 21 days.

(21) Appl. No.: 16/584,872

(22) Filed: Sep. 26, 2019

(65) Prior Publication Data
US 2020/0103481 A1  Apr. 2, 2020

(30) Foreign Application Priority Data
Sep. 27, 2018  (EP) .................................. 18197190

(51) Int. Cl.
| | | |
|---|---|---|
| *G01R 33/54* | (2006.01) | |
| *A61B 5/055* | (2006.01) | |
| *G01R 33/48* | (2006.01) | |
| *G01R 33/50* | (2006.01) | |
| *G01R 33/56* | (2006.01) | |
| *G01R 33/561* | (2006.01) | |

(52) U.S. Cl.
CPC ............ *G01R 33/543* (2013.01); *A61B 5/055* (2013.01); *G01R 33/4828* (2013.01); *G01R 33/50* (2013.01); *G01R 33/561* (2013.01); *G01R 33/5608* (2013.01)

(58) Field of Classification Search
USPC ........................................................ 324/309
See application file for complete search history.

(56) References Cited

U.S. PATENT DOCUMENTS

| | | |
|---|---|---|
| 9,633,455 B1 | 4/2017 | Mailhe et al. |
| 10,162,031 B2 | 12/2018 | Tunnicliffe et al. |
| 10,634,748 B2 | 4/2020 | Irfanullah et al. |
| 2013/0271132 A1 | 10/2013 | Griswold |
| 2015/0301141 A1 | 10/2015 | Griswold et al. |
| 2015/0301142 A1 | 10/2015 | Griswold et al. |
| 2015/0302579 A1 | 10/2015 | Griswold et al. |
| 2016/0155238 A1 | 6/2016 | Bachschmidt et al. |
| 2016/0291107 A1 | 10/2016 | Rosen et al. |
| 2016/0299206 A1 | 10/2016 | Cohen |

(Continued)

OTHER PUBLICATIONS

Google Translation of European Search Report for European Application No. EP 18197190.4, dated Mar. 13, 2019. (Year: 2019).*

(Continued)

*Primary Examiner* — Rodney E Fuller
(74) *Attorney, Agent, or Firm* — Schiff Hardin LLP

(57) ABSTRACT

A magnetic resonance fingerprinting (MRF) method for determining parameter values in pixels of an examination object can use a magnetic resonance system with, for example, a constant magnetic field strength (e.g. of less than 1.5 tesla or a constant magnetic field strength of less than 0.5 tesla). The MRF method can be adapted for conditions that prevail with such low-field magnetic resonance systems, thus enabling the parameter values to be advantageously determined efficiently while simultaneously maintaining a high degree of quality.

16 Claims, 3 Drawing Sheets

(56) References Cited

U.S. PATENT DOCUMENTS

| | | |
|---|---|---|
| 2017/0003365 A1 | 1/2017 | Rosen et al. |
| 2017/0052240 A1 | 2/2017 | Lauer |
| 2017/0115368 A1 | 4/2017 | Chen et al. |
| 2017/0178319 A1 | 6/2017 | Sugiura |
| 2017/0309019 A1 | 10/2017 | Knoll et al. |
| 2018/0005417 A1 | 1/2018 | Schieke |
| 2018/0074145 A1 | 3/2018 | Kluge et al. |
| 2018/0074148 A1 | 3/2018 | Pfeuffer |
| 2018/0203082 A1 | 7/2018 | Griswold et al. |
| 2018/0217220 A1 | 8/2018 | Gulani et al. |
| 2018/0231626 A1 | 8/2018 | Gulani et al. |
| 2018/0268942 A1 | 9/2018 | Kamali-Zare et al. |
| 2018/0286041 A1 | 10/2018 | Hu et al. |
| 2018/0292493 A1 | 10/2018 | Griswold et al. |
| 2018/0321345 A1 | 11/2018 | Van Den Brink |
| 2019/0102516 A1 | 4/2019 | Schieke |
| 2019/0221314 A1 | 7/2019 | Hennig et al. |
| 2019/0340463 A1 | 11/2019 | Nittka et al. |
| 2019/0361080 A1 | 11/2019 | Nittka et al. |
| 2019/0377046 A1 | 12/2019 | Nickel |
| 2019/0383892 A1* | 12/2019 | Nittka ............... G01R 33/54 |
| 2020/0005497 A1 | 1/2020 | Arberet et al. |
| 2020/0041595 A1 | 2/2020 | Flask et al. |
| 2020/0096589 A1 | 3/2020 | Sommer et al. |
| 2020/0191893 A1 | 6/2020 | Grodzki |

OTHER PUBLICATIONS

Zhao Bo et al., "Optimal Experiment Design for Magnetic Resonance Fingerprinting", Conf Proc IEEE Eng Med Biol Soc, Aug. 2016: pp. 453-456.

Assländer, Jakob et al. "Pseudo Steady-State Free Precession for MR-Fingerprinting" Magnetic Resonance in Medicine (2016) // DOI: 10.1002/mrm.26202.

Koktzoglou et al., „Radial Fast Interrupted Steady-State (FISS) Magnetic Resonance Imaging, Magnetic Resonance in Medicine 79: S. 2077-2086, 2018.

Jiang, Yun et al. "MR Fingerprinting Using Fast Imaging with Steady State Precession (FISP) with Spiral Readout"; in Magnetic Resonance in Medicine; vol. 74; pp. 1621-1631, (2015); 2015.

Bhairav Bipin Menta et al; "Magnetic resonance fingerprinting: a technical review: Magnetic Resonance in Medicine"; Magnetic Resonance in Medicine., Bd. 81, Nr. 1, Sep. 14, 2018 (Sep. 14, 2018), Seiten 25-46, XP055562942, US ISSN: 0740-3194, DOI: 10.1002/mrm.27403.

Mathieu Sarracanie et al; "3D Balanced-EPI Magnetic Resonance Fingerprinting at 6.5 mT"; Proceedings of the International Society for Magnetic Resonance in Medicine, ISMRM, 23rd Annual Meeting and Exhibition, Toronto, Ontario, Canada, May 30-Jun. 5, 2015, Nr. 3385, May 15, 2015 (May 15, 2015), XP040669061.

Dan Ma et al., "Magnetic resonance fingerprinting", Nature. Mar. 14, 2013; 495(7440): pp. 187-192.

Mathieu Sarracanie et al.: "High Speed MR Fingerprinting at 6.5 mT", Proceedings of the International Society for Magnetic Resonance in Medicine, ISMRM, Joint Annual Meeting ISMRM-ESMRMB, Milan, Italy, May 10-16, 2014, Nr. 4289, Apr. 28, 2014 (Apr. 28, 2014), XP040671062.

European Search Report dated Mar. 4, 2019 for European Application No. 18197190.4.

German action dated Jun. 26, 2020, Application No. 10 2018 209 584.1.

* cited by examiner

LOW-FIELD MAGNETIC RESONANCE FINGERPRINTING

CROSS REFERENCE TO RELATED APPLICATIONS

This patent application claims priority to European Patent Application No. 18197190.4, filed Sep. 27, 2018, which is incorporated herein by reference in its entirety.

BACKGROUND

Field

The disclosure relates to a magnetic resonance fingerprinting method for low-field magnetic resonance systems for improved determination of local parameter values of an examination object.

Related Art

Magnetic resonance (MR) is a known technique with which images of the inside of an examination object can be generated. Expressed in a simplified manner, for this purpose the examination object is positioned in a magnetic resonance device in a comparatively strong static, homogeneous constant magnetic field, also called a B0 field, with field strengths of 0.2 tesla to 7 tesla and more, such that the nuclear spins thereof are aligned along the constant magnetic field. Radio-frequency excitation pulses (RF pulses) are irradiated into the examination object to trigger nuclear spin resonances and the triggered nuclear spin resonances are measured as what is known as k-space data on the basis of which MR images are constructed or spectroscopy data is ascertained. In addition to RF excitation pulses, to manipulate the spins in the examination object, further RF pulses can be irradiated, for example for refocusing or inversion of a magnetization state achieved by excitation. Herein, the radiated RF pulses only affect spins in the examination object of which the Larmor frequency (frequency of precession of the spins, resonance frequency) is in resonance with the frequency used for the RF pulses ("on-resonance").

In order to manipulate a sufficient number of spins with an RF pulse, generally the RF pulses used have a mid-frequency and a specific frequency bandwidth that cover the desired Larmor frequencies. During proton MR imaging, it is attempted, for example, to excite the Larmor frequencies of spins in water. If an RF pulse has an effect on a spin, its Larmor frequency lies within what is known as a passband of the RF pulse. If an RF pulse has no effect on a spin, its Larmor frequency lies within what is known as a stopband of the RF pulse. Since no usable RF pulse has an ideal profile, there is a transitional region between the passbands and stopbands in each case. In the case of the repeated use of RF pulses, after a repetition time TR in each case, such as is used with steady-stage pulse sequences, for example, it is in addition possible that off-resonance effects can result in the formation of a band structure in the signal response frequencies, which generates further stopbands within the actual passband possibly leading to the formation of what are known as banding artifacts. Herein, the band structure, i.e. an arrangement of the frequency ranges that form passbands and the frequency ranges that form stopbands, is dependent not only on the RF pulses used and the nature of their irradiation, but also on the relaxation properties of the examination object in question, for example the longitudinal relaxation T1 and transverse relaxation T2 of the tissue in the examination object.

For spatial encoding of the scan data, the constant magnetic field is superimposed with rapidly switched magnetic gradient fields defining the trajectories along which the scan data is read out in the k-space. The recorded scan data is digitized and stored as complex numerical values in a k-space matrix. An associated MR image can be reconstructed from the k-space matrix populated with values by means of a multidimensional Fourier transform, for example. A specifically ordered sequence of RF pulses to be irradiated, gradients to be switched and readout processes used for this purpose is called a pulse sequence.

Different types of pulse sequence are known that have different degrees of sensitivity to parameters describing the materials contained in the examination object in question (for example longitudinal relaxation T1, transverse relaxation T2 and proton density). Depending upon the sensitivities of the sequence type used, the MR images reconstructed from scan data recorded with a specific sequence type show weighted images of the examination object.

Magnetic resonance imaging by means of a magnetic resonance system can be used to determine the presence and/or distribution of a substance located within in an examination object. Herein, the substance can, for example, be potentially pathological tissue in the examination object, a contrast agent, a tracer substance or a metabolic product.

In this case there are numerous ways for obtaining information on the substances present from the recorded scan data. A relatively simple source of information for example is image data reconstructed from the scan data. However, there are also more complex methods, which, for example, ascertain information on the examination object in question from pixel time series of image data reconstructed from successive scan data records.

Quantitative MR imaging techniques can be used to determine absolute properties of the scanned object, for example the tissue-specific T1 and T2 relaxation in humans. In contrast to this, conventional sequences that are most often used in clinic routine only generate a relative signal intensity of different tissue types (known as weightings) such that the diagnostic interpretation is heavily dependent on subjective estimation by the radiologist. Hence, quantitative techniques have the evident advantage of objective comparability, but at present are hardly ever routinely used on account of the long scanning times.

Newer quantitative scanning methods, such as magnetic resonance fingerprinting methods (MRF methods), have been able to reduce the above-cited drawback of longer scanning times to an acceptable extent. In MRF methods, items of scan data are recorded in temporal sequence with different recording parameters. A series of image data is reconstructed from the successively recorded items of scan data. A signal characteristic for one of the pixels of the series of image data in each case is treated as a pixel time series. Herein, the signal characteristic can be examined for all pixels of the image data or at least for those of interest. Herein, such a signal characteristic of a pixel time series is often referred to as a "fingerprint" of the location in the examination object depicted in the respective pixel. A signal characteristic of this kind can be used to determine the parameters present in the location of the examination object depicted by the pixel during the scan.

For this purpose, these signal characteristics are compared by means of "pattern recognition" methods with signal characteristics in a previously ascertained database of characteristic signal characteristics for specific substances (known as the "dictionary"). Hence, the substances represented in the image data reconstructed from the scan data or the spatial distribution of tissue-specific parameters (such as transverse relaxation T2, effective transverse relaxation T2* or longitudinal relaxation T1; known as T2, T2* and T1 maps) can be ascertained in the mapped examination object. Herein, the signal characteristics contained in such a dictionary can also be created by simulation.

Hence, this method is based on the principle of comparing scanned signal characteristics with a multiplicity of previously known signal characteristics. Herein, signal characteristics can be ascertained for the dictionary for different combinations of T1 and T2 relaxation times and other parameters. Reference is made to a "dimension" of the dictionary for each parameter to be determined comprising different parameter values of the respective parameter in order to provide different comparative values. The parameter values, for example T1 and T2 times, of a pixel (pixel/voxel) in the image are in particular determined in that the scanned signal characteristic is compared with all or some of the simulated signal characteristics. This process is referred to as "matching". In known MRF methods, the signal characteristic in the dictionary that is most similar to the scanned signal characteristic determines the parameters, for example relaxation parameters T1 and T2, of the respective pixel. Such a determination of parameter values in conjunction with MRF techniques is also referred to as a reconstruction or reconstruction process.

Herein, in principle, in addition to the above-cited tissue-specific parameters of an examined object, it is also possible to ascertain scan-specific parameters, such as, for example, the field strengths of the applied magnetic fields or also the local distribution of the strength of an irradiated radio-frequency field B1, since signals recorded by means of MR techniques can be dependent upon tissue-specific parameters and scan-specific parameters present in the examined object which describe the conditions prevailing during the scan. Herein, the recording parameters used are selected such that the recorded scan data displays a dependence on the desired parameters to be determined. For example, sequence types used for the MRF method can be sensitive to the desired parameters. The dependencies and the variation in the recording parameters and the fact that they are taken into account in the stored comparison signal characteristics enable the desired parameters to be determined from pixel time series recorded in this way.

For MRF methods, it is in principle possible to use any echo technique (in particular spin echo (SE) techniques and gradient echo (GRE) techniques) in combination with any k-space sampling methods (for example Cartesian, spiral, radial).

An MRF method that takes account of the tissue-specific parameters T1 and T2 in the dictionary used and determines them in scanned pixel time series, is, for example, described in the article by Ma et al., "Magnetic Resonance Fingerprinting", Nature, 495: pp 187-192 (2013). Here, a TrueFISP ("true fast imaging with steady-state free precession") based sequence is used in combination with spiral k-space sampling.

Another MRF implementation is described by Jiang et al. in the article "MR Fingerprinting Using Fast Imaging with Steady State Precession (FISP) with Spiral Readout", Magnetic Resonance in Medicine 74: pp 1621-1631, 2015. Here, an FISP sequence ("fast imaging with steady state precession") is used in combination with spiral sampling: after an adiabatic 180° RF inversion pulse for targeted disruption of the steady state of the spins, a sequence of RF excitation pulses with pseudorandomized flip angles is applied and every echo resulting in each case after one of the RF excitation pulses is read out with an individual spiral k-space trajectory. The n RF excitation pulses used generate the same number of echoes. An individual image is reconstructed from the scan data of each echo recorded along the respective k-space trajectory. A signal characteristic is extracted from the n individual images for each pixel and compared with the simulated characteristics. Here, the time interval TR between two successive RF excitation pulses of the n RF excitation pulses can also be varied, for example pseudorandomized.

In view of the multiplicity of variable parameters, it is not easy to determine an optimal procedure for MRF methods. However, several experiments have already been performed with the aim of optimizing MRF methods. Thus, one approach is known from the article by Zhao Bo et al, "Optimal Experiment Design for Magnetic Resonance Fingerprinting", Conf. Proc. IEEE Eng. Med. Biol. Soc., 2016, for example, which attempts to optimize the coding of signals to be recorded for a fingerprint, and hence the pixel time series created, with reference to the variation of the imaging parameters required with MRF, and hence the required number of signals to be recorded for each fingerprint, on the one hand, and the ability of the fingerprints to quantify different parameters, on the other. A method for optimizing the sampling scheme used with MRF methods, i.e. for improving the recording of the MR raw data with MRF, is, for example, described in the patent application US20180074145A1.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
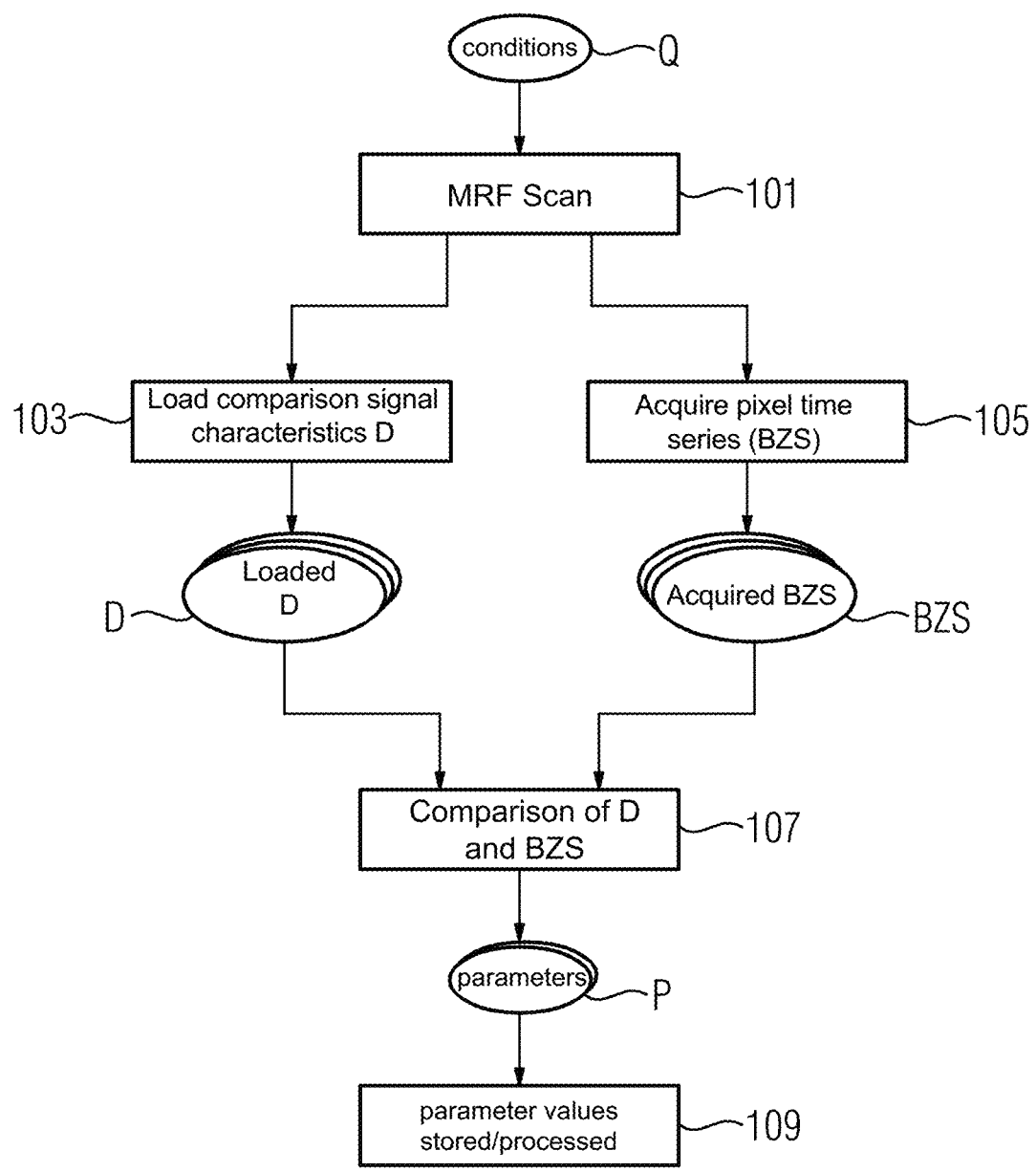
FIG. 1 is a flowchart of a method according to an exemplary embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure.

An object of the present disclosure is to enable an efficient quantitative determination of parameters using magnetic resonance fingerprinting (MRF) with high-quality results.

In an exemplary embodiment, a method according to the disclosure for determining parameter values in pixels of an examination object using a magnetic resonance fingerprinting (MRF) technique includes:

loading previously created comparison signal characteristics (D), acquisition of at least one pixel time series (BZS) of the examination object with the aid of an MRF recording method on a low-field magnetic resonance system, determination of the values (P) of the parameters to be determined based on signal comparisons of at least one segment of the respective signal characteristic of the acquired pixel time series (BZS) with a corresponding segment of the loaded comparison signal characteristics (D), storing and/or outputting the values (P) of the parameters to be determined that are determined for the respective pixel.

To date, no methods are known that use MRF with low-field magnetic resonance systems. Here, low-field magnetic resonance systems should be understood to mean magnetic resonance systems with constant magnetic field strengths of less than 1.5 tesla, preferably less than 0.5 tesla.

Low-field magnetic resonance systems are inexpensive and, unlike magnetic resonance systems with higher constant magnetic field strengths (from about 1.5 tesla), do not mandatorily require superconducting magnets, as a result of which they occupy less space and are easier to handle.

The disclosure proposes an MRF method for determining parameter values in pixels of an examination object for magnetic resonance systems with a constant magnetic field strength of less than 1.5 tesla, preferably with a constant magnetic field strength of less than 0.5 tesla. The MRF method can be adapted for the conditions that prevail with low-field magnetic resonance systems of this kind, thus enabling the parameter values to be determined particularly efficiently while simultaneously maintaining a high degree of quality.

In low-field magnetic resonance systems, there can be a high degree of homogeneity of the constant magnetic field actually achieved. Moreover, on account of the lower constant magnetic field strength, the load on an examination object defined by the specific absorption rate (SAR) is reduced compared to systems with higher constant magnetic field strengths, thus allowing more room for maneuver with respect to the RF pulses that are also included in the SAR value, enabling transmit fields B1 with higher amplitudes to be irradiated.

During the creation of the comparison signal characteristics for an MRF method according to the disclosure, at least one scan-specific parameter from the group including the field strength of a constant magnetic field B0 present during the recording of the MR raw data and the field strength of a transmit field B1 present during the recording of the MR raw data can be left out of account. As a result of the omission of the dimension of the constant magnetic field B0 and/or the dimension of the transmit field B1, a dictionary created in this way from stored comparison signal characteristics is much smaller than dictionaries containing these dimensions. Consequently, the computing effort required for the matching to be performed and the time required for the MRF method are greatly reduced.

Instead of completely omitting at least one of the dimensions 'constant magnetic field B0' and 'transmit field B1' during the creation of the comparison signal characteristics of the dictionary, it is also possible to take account of at least one scan-specific parameter from the group including the field strength of a constant magnetic field B0 present during the recording of the MR raw data and the field strength of a transmit field B1 present during the recording of the MR raw data to a lesser extent. For example, the variation of at least one of the scan-specific parameters, i.e. the range from which values for a comparison signal characteristic are provided, can be selected as small. For this purpose, it is for example possible to select a variation of maximum 20 percent (for example ±10 percent), preferably maximum 5 percent (for example ±2.5 percent) from an expected relative value (corresponding to 100 percent).

The variation in one of the above-cited parameter values can also be selected as small in comparison to a variation in tissue-specific parameters used during the creation of the comparison signal characteristics. Additionally or alternatively, a number of parameter values for which comparison signal characteristics are created during the creation of the comparison signal characteristics for at least one of the scan-specific parameters can be selected as much smaller than a number of parameter values for a tissue-specific parameter for the comparison signal characteristics. During the creation of the comparison signal characteristics, it is also possible for a selected resolution of the parameter values in a selected parameter range, i.e. in particular the number of parameter values used for the creation of the comparison signal characteristics, to be selected as much smaller for at least one scan-specific parameter than a resolution of tissue-specific parameters.

Thus, during the creation of the comparison signal characteristics, with reference to the number of parameter values used, variation and/or resolution, at least one of the scan-specific parameters can only be taken into account by maximum 20 percent, preferably maximum 5 percent, in comparison to tissue-specific parameters taken into account during the creation of the comparison signal characteristics (=100 percent taken into account). This results in a significant reduction in the size of the dictionary and hence also reduces the computing effort and computing time required for the MRF method.

If, for example, approximately 50 to 80 or even 100 different values are taken into account for tissue-specific parameters such as transverse relaxation and longitudinal relaxation during the creation of the comparison signal characteristics, 10 or fewer different values can be used for the above-cited scan-specific parameters.

Although the results of MRF methods are greatly dependent upon the parameters taken into account during the creation of the dictionary and how precisely and hence with which parameters and in which parameter range with which resolution of possible parameter values, comparison signal characteristics were created, despite the reduction in the size of the dictionary, the use of a low-field magnetic resonance system can maintain a high-quality determination of the parameter values in that, for example, the degree of such a reduction in the size of the dictionary is decided in accordance with the homogeneity of the constant magnetic field B0 effected by the low-field magnetic resonance system and the homogeneity of the transmit field B1 effected by the low-field magnetic resonance system. This enables the creation of the comparison signal characteristics of the dictionary for the MRF method to be performed to be adapted to the conditions applicable with respect to the low-field magnetic resonance system used, in particular the hardware conditions thereof, thus enabling optimal use to be made of the specific conditions applicable with respect to low-field magnetic resonance systems.

The pulse sequence used to record the MR raw data can be a pulse sequence of a balanced steady-state free precession (bSSFP; also called TrueFISP) pulse sequence type. In particular, the MR raw data can be mainly or even exclusively recorded by means of pulse sequences of the bSSFP pulse sequence type. bSSFP pulse sequences permit quick recording of MR raw data with an intrinsically high signal-to-noise ratio (SNR). In addition, bSSFP pulse sequences are sensitive to both longitudinal and the transverse relaxation and hence pixel time series obtained by means of bSSFP pulse sequences are easy to distinguish, i.e. these two parameters can be determined with a high degree of precision from pixel time series obtained by means of bSSFP pulse sequences by comparison with a corresponding dictionary. In addition, recording of the MR raw data with a low-field magnetic resonance system according to the disclosure avoids what are known as "banding artifacts" that otherwise frequently occur with bSSFP pulse sequences, for example induced by inhomogeneities in the constant magnetic field. Despite a low constant magnetic field strength, the intrinsically high SNR of bSSFP pulse sequences enables a good signal quality to be achieved.

Herein, the MR raw data can be recorded along Cartesian, radial or spiral k-space trajectories. Very short repetition times $TR_i$, are possible in conjunction with a Cartesian or radial sampling scheme, which keeps the scanning time short. Short repetition times $TR_i$ are also conceivable in conjunction with spiral sampling of the k-space. As a result of the short readout time of spiral k-space trajectories used to record signals to be stored as MR raw data and the high homogeneity of the constant magnetic field B0 with low-field magnetic resonance systems, the spiral blurring effect that would be otherwise expected is only low and hence few if any spiral blurring artifacts occur.

The flip angles, echo times and/or repetition times used to record the MR raw data were optimized such that the excited spins were present in a pseudo steady state. Such optimization is described in the article by Assländer et al., "Pseudo Steady-State Free Precession for MR-Fingerprinting," Magnetic Resonance in Medicine 77: pp 1151-1161, 2017. Establishing a pseudo steady state of magnetization in this way restores the spin echo nature of the echo signals generated for MRF.

In the context of the method according to the disclosure, acquired pixel time series can be created from MR raw data recorded by means of a pulse sequence including RF pulses to be irradiated and gradients to be switched, for which the repetition times applied are selected such that stopbands are avoided within an excitation region excited by the pulse sequence in the examination object. This achieves a high degree of robustness with respect to flux and movement within the target volume, for example a slice. Recording the MR raw data for the MRF method with low-field magnetic resonance systems with repetition times $TR_i$ selected such that stopbands, and hence artifacts induced by off-resonance effects, are avoided provides high-quality recorded MR raw data. Stopbands are, for example, reduced in that the repetition time TR is reduced, as a result of which passbands, and also any possible sidebands, are widened.

For example, for this purpose, the repetition times $TR_i$ can be selected such that the central passband of the pulse sequence used, for example TrueFISP-based pulse sequence, is wide enough to hold as many spins as possible in the examination to be mapped in the central passband. To this end, the repetition times $TR_i$ can in particular be selected short enough that the central passband of the pulse sequence with a width proportional to $1/TR_i$ achieves the width necessary to this purpose.

For the recording of the MR raw data, the repetition time $TR_i$ can in particular be selected such that a passband, in particular the central passband, of the RF pulses used during recording of the MR raw data is wide enough to enable both spins of a first spin species present in the examination object and spins of a second spin species present in the examination object to lie in the passband, wherein the first spin species has a different resonance frequency than that of the second spin species. In this way, it is possible to avoid the possibility of the signal of one spin species being too low. The repetition time can only influence the width of the passbands, but not the location of passbands in the frequency range.

To set the location of the passbands, the phase cycle of RF pulses used during the recording of the MR raw data can be selected such that both spins of a first spin species present in the examination object and spins of a second spin species present in the examination object are excited in a passband, in particular the central passband, wherein the first spin species has a different resonance frequency than that of the second spin species.

The first and the second spin species can, for example, be selected from the group with the spin species fat and water, which have different resonance frequencies. The difference between the resonance frequencies of fat and water is inter alia referred to as "chemical shift". This is linearly dependent upon the field strength, wherein the difference is less at low frequencies. Therefore, low-field MR has the advantage that it is easier to find short TRs with which fat and water lie in the central passband.

A magnetic resonance system according to the disclosure includes a magnet unit, a gradient unit, a radio-frequency unit and a control facility with a parameter-value-determiner embodied to carry out a method according to the disclosure.

A computer program according to the disclosure implements a method according to the disclosure on the control facility when it is executed on the control facility.

Herein, the computer program can also be present in the form of a computer program product, which can be loaded directly into a memory of a control facility, with program code means for carrying a method according to the disclosure when the computer program product is executed in the processor of the computing system.

An electronically readable data carrier according to the disclosure includes electronically readable control information stored thereupon, which includes at least one computer program according to the disclosure and is embodied such that it carries out a method according to the disclosure when the data carrier is used in a control facility of a magnetic resonance system.

The advantages and embodiments disclosed with respect to the method also apply analogously to the magnetic resonance system, the computer program and the electronically readable data carrier.

FIG. 1 is a schematic flow diagram of a method according to the disclosure for determining parameter values in pixels of an examination object by means of a magnetic resonance fingerprinting (MRF) technique.

Herein, previously created comparison signal characteristics D are loaded (block 103).

At least one pixel time series BZS is acquired (block 105) using an MRF recording method on a low-field magnetic resonance system with a constant magnetic field of less than 1.5 tesla, preferably with a constant magnetic field of less than 0.5 tesla.

As is usual with MRF methods, values P of the parameters to be determined, such as, for example, the local values for longitudinal relaxation or transverse relaxation corresponding to the pixel, are determined based on signal comparisons (in particular in the context of an MRF matching method) of at least one segment of the respective signal characteristic of an acquired pixel time series BZS with a corresponding segment of the loaded comparison signal characteristics D (block 107).

The determined values P of the parameters to be determined can be stored and/or further processed (block 109), for example output in the form of a parameter map on a display apparatus such as a display screen.

During both the creation of the comparison signal characteristics D in block 103, and the acquisition of the pixel time series BZS in block 105, it is possible to take account of the conditions Q applicable during the MRF scan to be performed (block 101). Such conditions can in particular be hardware properties of the magnetic resonance system on which the MRF scan is to be performed, such as, for example, properties from the group including constant magnetic field strength and gradient properties, such as the possible ramp speed and possible gradient strength. The conditions Q can, for example, as described above, be used as the basis for the definition of the dimensions (the parameters which are to be varied) and the size of the respective dimensions (the range and resolution with which the respective parameters will be varied). Furthermore, the selection of the pulse-sequence parameters to be used with the MRF method, for example flip angles, repetition times, echo times, can be optimized on the basis of the conditions Q.

Herein, in particular as described above, at least one scan-specific parameter forming a dimension of the dictionary can be left out of account or only taken into account to a small extent during the creation of the comparison signal characteristics of the dictionary.

Hence, during the creation of the comparison signal characteristics, at least one scan-specific parameter from the group including the field strength of a constant magnetic field B0 present during the recording of the MR raw data and the field strength of a transmit field B1 present during the recording of the MR raw data can be left out of account.

Similarly, during the creation of the comparison signal characteristics, at least one scan-specific parameter from the group including the field strength of a constant magnetic field B0 present during the recording of the MR raw data and the field strength of a transmit field B1 present during the recording of the MR raw data can be taken into account to a much lesser extent than tissue-specific parameters.

It is not only the dictionary used with its stored comparison signal characteristics that can be configured particularly efficiently for low-field magnetic resonance systems. The encoding of the signals to be recorded as MR raw data can also be configured for low-field magnetic resonance systems such that high signal quality, in particular particularly low susceptibility to artifacts, is achieved.

For example, acquired pixel time series BZS can be created from MR raw data recorded by means of a pulse sequence including RF pulses to be irradiated and gradients to be switched with which, as described above, the repetition times $TR_i$ applied are selected such that stopbands are avoided within an excitation region excited by the pulse sequence in the examination object.

The pulse sequence used to record the MR raw data can be a pulse sequence of a bSSFP pulse sequence type, also called a TrueFISP-type pulse sequence. In addition to the above-described advantages, this also permits very short repetition times, for example repetition times of significantly below 10 milliseconds, for example repetition times of only 2 milliseconds, and hence the passbands of the RF pulses can be set particularly wide.

The MR raw data from which the pixel time series are created can be recorded along Cartesian, radial or spiral k-space trajectories. The selection of the k-space trajectories to be used can, for example, be made dependent upon the respective sampling schemes, individual artifact susceptibilities and the desired signal quality.

As described above, the selection of the flip angles, echo times and/or repetition times used to record the MR raw data can be optimized such that, during the recording of the MR raw data, the excited spins are present in a pseudo steady state. This can, for example, improve the distinguishability of different values for longitudinal relaxation. The method described for this purpose in the above-mentioned article by Assländer et al. functions in the central passband of the pulse sequence used of which the width, as already described, can be set particularly wide by the selection of the repetition times $TR_i$.

The selection of the repetition times $TR_i$ used, for example by restriction to low values, can enable the passbands of the RF pulses used to be set sufficiently wide that a passband, in particular the central passband of the RF pulses used during the recording of the MR raw data, is wide enough to enable both spins of a first spin species present in the examination object and spins of a second spin species present in the examination object to be excited in a passband, in particular the central passband, wherein the first spin species has a different resonance frequency than that of the second spin species. Thus, destructive signal superimpositions and hence artifacts are avoided, wherein optimally the MR raw data contains signals of both spin species simultaneously. The width of the passband is less than the inverse value of the repetition time TR used ("maximum desired resonance frequency"–"minimum desired resonance frequency"<1/TR).

Herein, additionally or alternatively, the phase cycle and/or the frequency, in particular the mid-frequency and/or the bandwidth, of the RF pulses used during the recording of the MR raw data can be selected such that both spins of a first spin species present in the examination object and spins of a second spin species present in the examination object are excited in a passband, in particular the central passband, wherein the first spin species has a different resonance frequency than that of the second spin species. Such a selection of the phase cycle and/or frequency of the RF pulses used may itself be sufficient to cover the resonance frequencies of both desired spin species in the passband. In any case, such a selection can have the result that the width of the passband does not have to be set unnecessarily wide, but the range of the desired resonance frequencies (maximum resonance frequency to minimum frequency in the examination object) is still covered.

If it is not desired or possible to record the signals from two different spin species, it is also possible for the signals from one of the two spin species to be suppressed. This is explained in more detail below with reference to FIG. 2.

Figure 2:
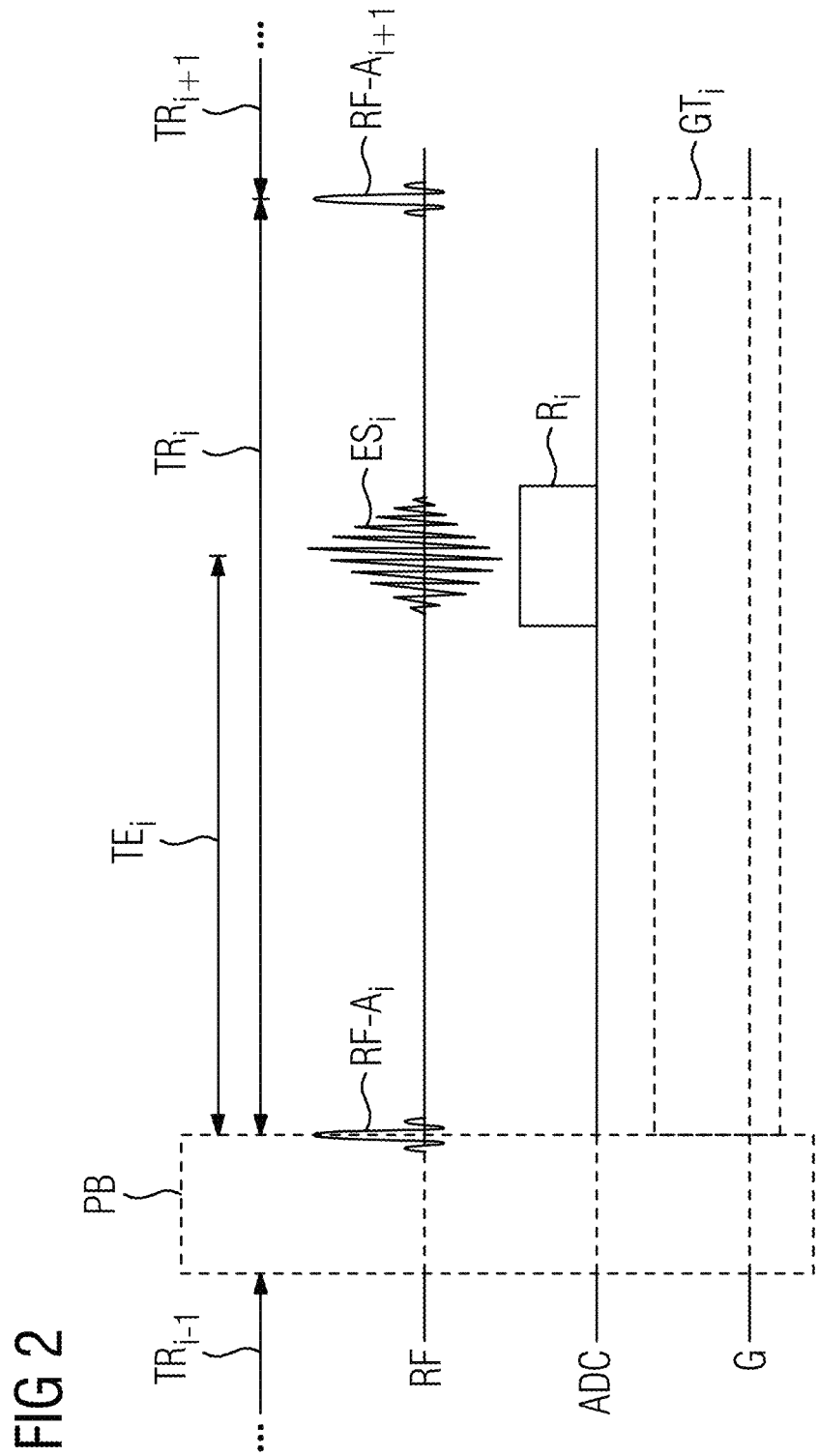
FIG. 2 is a schematic pulse sequence diagram illustrating pulse sequences according to an exemplary embodiment of the present disclosure.

FIG. 2 depicts a rough schematic example of suitable pulse sequences in a pulse sequence diagram. Here, the pulse sequence generally designates the scheme of a temporal sequence of RF pulses to be irradiated and gradients to be switched which are used to generate and read out MR signals from an examination object. Hence, in accordance with the pulse sequence, RF pulses are irradiated into an examination object, gradients are switched and echo signals generated by the irradiated RF pulses and the switched gradients are read out.

The uppermost line (RF) depicts the radio-frequency activity. Within a repetition time $TR_i$, at least one excitation pulse $RF-A_i$ is irradiated and, after an echo time $TE_i$ after the excitation pulse $RF-A_i$, an echo signal $ES_i$ is read out in a readout period $R_i$ as MR raw data (ADC). Depending on the pulse sequence, it is also possible for further RF pulses to be switched between the excitation pulse $RF-A_i$ and the echo signal $ES_i$, but these are not shown for purposes of simplicity. Within a repetition time $TR_i$, a gradient train $GT_i$, which can include gradients in all gradient directions G, is switched; once again, the exact embodiment thereof is dependent upon the type of pulse selected for this repetition, for example a gradient echo sequence, a spin echo sequence or a steady-state sequence, and the k-space trajectory, along which the MR raw data can be read out. The gradients to be switched for the different known pulse sequence types are known in principle to the person skilled in the art; for example in the case of a pulse sequence of the type of a balanced steady-state free precession (bSSFP), during the repetition time $TR_i$, the gradient train $GT_i$ would be embodied such that the zeroth moment of all of the gradients associated with the bSSFP sequence is compensated. In other words, the zeroth moment disappears between two successive RF excitation pulses $RF-A_i$ and $RF-A_i$ and $RF-A_{i+1}$. In FIG. 2, the gradient train $GT_i$ is only indicated by a box for purposes of simplicity. After a repetition time $TR_i$, which can vary according to the disclosure, for example as in the above-cited article by Assländer et al., a new pulse sequence is started in order to record further MR raw data, as indicated by the following excitation pulse $RF-A_{i+1}$, wherein in each repetition i, other gradients in the gradient train $GT_i$ can be switched and/or other RF pulses can be irradiated and wherein it is also possible for different pulse sequence types to be used in different repetitions i.

In MRF methods, a flip angle of irradiated RF pulses, in particular the excitation pulse $RF-A_i$, can be varied in each repetition time $TR_i$. In MRF methods, overall N repetitions i are performed (i=1, ..., N), wherein N is a natural number greater than one and, depending upon the application, can also be several hundred to several thousand thus enabling MR raw data to be recorded N-times. A signal value can be calculated for at least one pixel from each of the N recorded records of MR raw data, thus enabling a pixel time series of signal values recorded at N times to be obtained.

If required, a sequence of N such repetitions i can be interrupted by the insertion of preparation blocks. This is depicted in FIG. 2 by a preparation block PB inserted between the (i–1)-th and the i-th repetition. During a preparation block PB, the magnetization of the spins examined is prepared as desired. For this, further RF pulses can be irradiated and also further gradients switched. For example, an RF inversion pulse can be irradiated in order also to perform a spin preparation known by the umbrella term "inversion recovery" and, for example, to suppress signals from a selected spin species (for example fat or liquid). It is also possible to use preparation blocks PB to prepare a desired weighting, for example of a T1 or T2 preparation. Hence, the recording of the MR raw data can include preparation blocks.

Such preparation blocks PB can in particular be switched between repetitions (i–1) and i such that the sequence of N repetitions is interrupted periodically by a preparation block PB. Hence, the preparation blocks can be arranged periodically in time during the recording of the MR raw data. This enables the effect of the preparation blocks to be maintained, for example in each case over several repetitions i following a preparation block PB, wherein it is not necessary to switch a preparation block PB before every repetition i. Thus, for example, overall, the scanning time can be kept shorter and, for example, the steady states achieved are interrupted less frequently.

For example, the article by Koktzoglou et al., "Radial Fast Interrupted Steady-State (FISS) Magnetic Resonance Imaging", Magnetic Resonance in Medicine 79: pp 2077-2086, 2018, describes a method with which the insertion of interruptions enables residual transverse magnetization in the examination volume to be destroyed, (flux) artifacts to be avoided in pulse sequences of a bSSFP sequence type and the saturation of fat signals to be achieved.

However, it can also be advisable to arrange preparation blocks PB in a non-periodic manner.

If, during a recording of MR raw data, it is necessary to suppress signals from a spin species present in the examination object, for example the spin species fat, additionally or alternatively to the above-described preparation blocks PB, it is also possible to use binomial pulses, for example as RF excitation pulses, which are embodied such that, spectrally selectively, they do not act on the spin species to be suppressed. Such binomial pulses are known in principle. When binomial pulses are used to suppress signals from a spin species, overall the scanning time is not extended in the same way as with the insertion of preparation blocks PB.

The quality of the suppression achieved can be increased by combining different suppression techniques, for example by using binomial pulses and preparation blocks PB, and/or the frequency of preparation blocks PB required for a sufficient suppression by binomial pulses.

Figure 3:
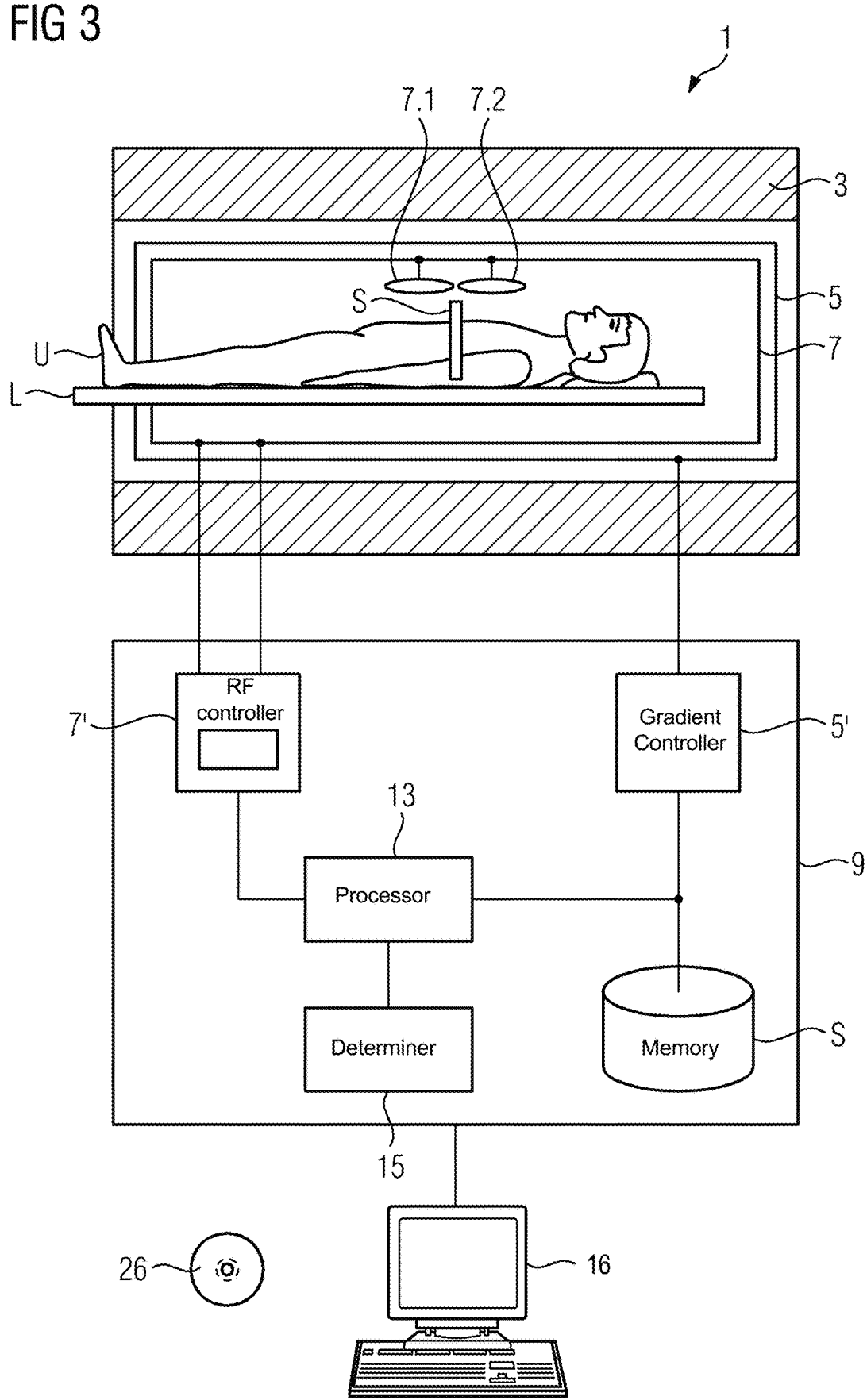
FIG. 3 is a magnetic resonance system according to an exemplary embodiment of the present disclosure.

FIG. 3 is a schematic depiction of a magnetic resonance system according to the disclosure 1. This includes a magnet unit 3 for generating the constant magnetic field, a gradient unit 5 for generating the gradient field, a radio-frequency unit 7 for irradiating and receiving radio-frequency signals and a control facility 9 embodied to carry out a method according to the disclosure.

FIG. 3 is a schematic depiction of these subunits of magnetic resonance system 1. In particular, the radio-frequency unit 7 can include a plurality of subunits, for example several coils like the schematically depicted coils 7.1 and 7.2, or more coils, which can be embodied only to send radio-frequency signals or only to receive the radio-frequency signals triggered or to do both.

For an examination of an examination object U, for example a patient or also a phantom, said object can be introduced into the scanning volume of the magnetic resonance system 1 on a bench L. The slice S represents an exemplary target volume of the examination object to be recorded from the scan data.

The control facility 9 is used to control the magnetic resonance system and can in particular control the gradient unit 5 by means of a gradient controller 5' and the radio-frequency unit 7 by means of a radio-frequency send/receive controller 7'. Herein, the radio-frequency unit 7 can include a plurality of channels on which signals can be sent or received. In an exemplary embodiment, the control facility 9 (and/or one or more of its components) includes processor circuitry that is configured to perform one or more operations and/or functions of the control facility 9, including controlling the magnetic resonance system 1 to obtain scan data and/or controlling the operations of one or more components of the control facility 9.

Together with its radio-frequency send/receive controller 7', the radio-frequency unit 7 is responsible for generating and irradiating (sending) an alternating radio-frequency field for manipulating the spins in a region to be manipulated (for example in slices to be scanned S) of the examination object U. Herein, if possible, the mid-frequency of the alternating radio-frequency field, also referred to as the B1 field, is generally ideally set close to the resonance frequency (Larmor frequency) of the spins to be manipulated. To generate the B1 field (transmit field), controlled currents are applied to the RF-coils in the radio-frequency unit 7 by means of the radio-frequency send/receive controller 7'. In an exemplary embodiment, the RF controller 7' includes processor circuitry that is configured to control currents applied to the RF-coils in the RF unit 7.

The control facility 9 further includes a parameter-value determiner 15 with which signal comparisons according to the disclosure for determining parameter values can be performed. Overall, the control facility 9 is embodied to carry out a method according to the disclosure. In an exemplary embodiment, the determiner 15 includes processor circuitry that is configured to perform signal comparisons to determine parameter values.

A processor 13 included by the control facility 9 is embodied to carry out all the computing operations required for the necessary scans and determinations. Interim results and results required for this purpose can be stored in a memory storage unit S of the control facility 9. The memory storage unit S is any well-known volatile and/or non-volatile memory. Herein, the units depicted should not necessarily be understood to be physically separate units, but only represent a subcategorization into coherent units, but which can also for example be implemented in a few or only one single physical unit. In an exemplary embodiment, the processor 13 includes processor circuitry that is configured to perform one or more computing operations required for the necessary scans and determinations.

An input/output (I/O) facility 16 of the magnetic resonance system 1 can be used by a user, for example, to route control commands to the magnetic resonance system and/or to display results of the control facility 9 such as, for example, image data. In an exemplary embodiment, the I/O facility 16 is a computer, mobile communication device (e.g. smartphone, tablet), or another stationary or mobile computing device as would be understood by one of ordinary skill in the relevant arts.

A method described herein can also in be present in the form of a computer program product including a program and which implements the described method on a control facility 9 when it is executed on the control facility 9. Similarly, an electronically readable memory storage medium 26 can be provided with electronically readable control information stored thereupon. The memory storage medium 26 can include at least one computer program product as described above and is embodied such that that it carries out the described method when the memory storage medium 26 is used in a control facility 9 of a magnetic resonance system 1. In exemplary embodiment, the memory storage medium 26 is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM).

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for determining parameter values in pixels of an examination object using a magnetic resonance fingerprinting (MRF) technique, the method comprising:
   loading previously created comparison signal characteristics;
   acquiring, by a MRF recording method on a low-field magnetic resonance (MR) scanner, at least one pixel time series of the examination object, the at least one acquired pixel time series being created from MR raw data recorded by a pulse sequence comprising irradiated radio-frequency (RF) pulses and switched gradients, for which repetition times applied are selected such that stopbands are avoided within an excitation region excited by the pulse sequence in the examination object;
   determining the parameter values based on a signal comparison of at least one segment of a respective signal characteristic of the acquired at least one pixel time series with a corresponding segment of the loaded comparison signal characteristics; and
   providing, as an output of the MR scanner, an electronic signal representing the determined parameter values for the respective pixel.

2. The method as claimed in claim 1, wherein, during creation of the comparison signal characteristics, at least one scan-specific parameter, from a group comprising a field strength of a constant magnetic field B0 present during recording of MR raw data and a field strength of a transmit field B1 present during the recording of the MR raw data, is excluded from consideration.

3. The method as claimed in claim 1, wherein, during creation of the comparison signal characteristics, an influence of at least one scan-specific parameter, from a group comprising a field strength of a constant magnetic field B0 present during recording of the MR raw data and a field strength of a transmit field present during the recording of the MR raw data, is minimized.

4. The method as claimed in claim 1, wherein a pulse sequence used to record the MR raw data in the acquisition of the at least one pixel time series is a pulse sequence of a balanced steady-state free precession pulse sequence type.

5. The method as claimed in claim 1, wherein the MR raw data recorded in the acquisition of the at least one pixel time series is recorded along Cartesian, radial or spiral k-space trajectories.

6. The method as claimed in claim 1, wherein flip angles, echo times, and/or repetition times used to record the MR raw data in the acquisition of the at least one pixel time series are optimized such that excited spins are present in a pseudo steady state.

7. The method as claimed in claim 1, wherein the repetition time is selected such that a width of a passband of the pulse sequence used during the recording of the MR raw data enables both spins of a first spin species present in the examination object and spins of a second spin species present in the examination object to be excited in the passband, wherein the first spin species has a different resonance frequency than that of the second spin species.

8. The method as claimed in claim 1, wherein a phase cycle of RF pulses used during recording of the MR raw data in the acquisition of the at least one pixel time series is selected such that both spins of a first spin species present in the examination object and spins of a second spin species present in the examination object are excited in a passband, wherein the first spin species has a different resonance frequency than that of the second spin species.

9. The method as claimed in claim 1, wherein signals from a spin species present in the examination object are suppressed during recording of the MR raw data in the acquisition of the at least one pixel time series.

10. The method as claimed in claim 9, wherein the recording of the MR raw data comprises using binomial pulses to suppress the signals.

11. The method as claimed in claim 9, wherein, to suppress the signals, the recording of the MR raw data comprises preparation blocks configured to prepare a desired magnetization, the preparation blocks being arranged periodically in time.

12. A computer program product having a computer program which is directly loadable into a memory of a controller of the magnetic resonance system, when executed by the controller, causes the magnetic resonance system to perform the method of claim 1.

13. A non-transitory computer-readable storage medium with an executable computer program stored thereon, that when executed, instructs a processor to perform the method of claim 1.

14. A magnetic resonance (MR) system comprising:
   a MR scanner configured to perform a magnetic resonance fingerprinting (MRF) recording method to acquire at least one pixel time series of an examination object, the at least one acquired pixel time series being created from MR raw data recorded by a pulse sequence comprising irradiated radio-frequency (RF) pulses and switched gradients, for which repetition times applied are selected such that stopbands are avoided within an excitation region excited by the pulse sequence in the examination object; and
   a controller that is configured to:
      load previously created comparison signal characteristics;
      determine a parameter values of the examination object based on a signal comparison of at least one segment of a respective signal characteristic of the acquired at least one pixel time series with a corresponding segment of the loaded comparison signal characteristics; and
      provide, as an output, an electronic signal representing the determined parameter values for the respective pixel.

15. The MR system as claimed in claim 14, wherein:
   the MR scanner comprise a magnet unit configured to generate a magnetic field, a gradient unit configured to generate a gradient field, and a RF unit configured to irradiate and receive RF signals; and
   the controller comprises a RF controller configured to control the RF unit to control currents applied to RF coils of the RF unit, and a parameter-value-determiner configured to compare the at least one segment of the respective signal characteristic of the acquired at least one pixel time series with the corresponding segment of the loaded comparison signal characteristics to determine the parameter values.

16. A method for determining parameter values in pixels of an examination object using a magnetic resonance fingerprinting (MRF) technique, the method comprising:
   loading previously created comparison signal characteristics;
   acquiring, by a MRF recording method on a low-field magnetic resonance (MR) scanner, at least one pixel time series of the examination object, wherein signals from a spin species present in the examination object are suppressed during recording of MR raw data in the acquisition of the at least one pixel time series;

determining the parameter values based on a signal comparison of at least one segment of a respective signal characteristic of the acquired at least one pixel time series with a corresponding segment of the loaded comparison signal characteristics; and providing, as an output of the MR scanner, an electronic signal representing the determined parameter values for the respective pixel.

* * * * *